United States Patent [19]

Fritzberg et al.

[11] Patent Number: 4,965,392

[45] Date of Patent: Oct. 23, 1990

[54] CHELATING COMPOUNDS FOR METAL-RADIONUCLIDE LABELED PROTEINS

[75] Inventors: Alan R. Fritzberg, Edmonds; Sudhakar Kasina, Kirkland; Tripuraneni N. Rao, Mill Creek; Jean-Luc VanderHeyden, Seattle; Ananthachari Srinivasan, Kirkland, all of Wash.

[73] Assignee: NeoRx Corporation, Seattle, Wash.

[21] Appl. No.: 172,004

[22] Filed: Mar. 23, 1988

Related U.S. Application Data

[63] Continuation-in-part of Ser. No. 31,440, Mar. 26, 1987, abandoned.

[51] Int. Cl.$^5$ .................. C07C 69/62; C07C 327/06
[52] U.S. Cl. ............................ 558/254; 560/145; 424/1.1
[58] Field of Search ................... 424/1.1; 534/14; 558/254; 560/145

[56] References Cited

U.S. PATENT DOCUMENTS

4,671,958 6/1987 Rodwell et al.
4,741,900 5/1988 Alvarez et al.
4,861,869 8/1989 Nicolotti et al.

FOREIGN PATENT DOCUMENTS

EP0173424 3/1986 European Pat. Off.
EP0188256 7/1986 European Pat. Off.

OTHER PUBLICATIONS

Fritzberg et al., "Synthesis and Biological Evaluation of Technetium-99m MAG$_3$ as a Hippuran Replacement", J. Nuc. Med., vol. 27, No. 1, Fritzberg et al. (I), Jan. 1986.
Fritzberg et al., "Synthesis and Characterization of Re and Tc Complexes of N2S2 and N3S Ligands", Sixth International Symposium on Radio-pharmaceutical Chemistry, 1986 (Fritzberg et al. II).
Nosco et al., "Characterization of the New [Tc-99m] Dynamic Renal Imaging Agent: [Tc-99m] MAG$_3$." J. Nuc. Med., vol. 27, No. 6, Jun., 1986, p. 939, Abstract No. 256.
Verbruggen et al., "Relation Between Structure and Renal Transport of Isomeric Methylderivatives of Tc-99m Mercaptoacetyltriglycine", J. Nuc. Med., vol. 27, No. 6, Jun., 1986, p. 894, Abstract No. 76.
Taylor et al., "Preliminary Evaluation of 99m Tc Mercaptoacetyltriglycine as a Replacement for $^{131}$ I OIH" Contr. Nephrol., vol. 56,5 (Taylor et al. II).
Taylor et al., "Comparison of Tc-99m Mercaptoacetyltriglycine (MAG$_3$) and OIH in Normal Subjects and Patients", J. Nuc. Med., vol. 27, No. 6, Jun., 1986, p. 962, Abstract No. 351 (Taylor et al. I).
Taylor et al., "Preliminary Evaluation of Technetium-99m Mercaptoacetyltriglycine (MAG$_3$) as a Replacement for Iodine-131OIH." J. Nuc. Med., vol. 27, No. 4, Apr. 1986, Taylor et al. III.
Muller-Suur et al., "Clearance and Renal Extraction of a New Renal Scanning Agent: Technetium-99m MAG$_3$ in Comparison to Hippurate (OIH) and EDTA. C." J. Nuc. Med., vol. 26, No. 4, Apr. 1986.
deJong et al., "Results of ERBF and ERPF Measurements in Healthy Dogs with Two New Radiopharmaceutical Principles." J. Nuc. Med., vol. 27, No. 4, Apr. 1986.
Bubeck et al., "Clinical Comparison of I-131 o-Iodohippurate with Tc-99m CO$_2$-DADS-A and Tc-99m MAG$_3$ by Simultaneous Double Tracer Measurement." Alsfelder Strasse 10.6100 Darmstadt Nuc Compact 17 (1986) 135-138.
T. W. Greene, "Protective Groups in Organic Synthesis", John Wiley and Sons, New York, New York, pp. 204-209 and 216-217.

*Primary Examiner*—John S. Maples

[57] ABSTRACT

Chelated radionuclide compositions are provided for conjugation to polypeptides and carbohydrates. The resulting conjugates may be used in diagnosis and therapy. Chelating compounds are disclosed.

6 Claims, 1 Drawing Sheet

| Compound | PG | R | R' | R" |
|---|---|---|---|---|
| A | THP | H | H | COOTFP |
| B | EOE | H | H | COOTFP |
| C | EOE | H | H | CH$_2$-CH$_2$-COOTFP |
| D | i-PrCO | CH$_2$-COOH | H | CH$_2$-CH$_2$-COOTFP |
| E | i-PrCO | CH$_2$-COOH | CH$_2$-COOH | CH$_2$-CH$_2$-COOTFP |
| F | i-PrCO | CH$_2$-CH$_2$-COOH | CH$_2$-COOH | CH$_2$-CH$_2$-COOTFP |
| G | Acm | H | H | COOH |
| H | Acm | CH$_2$-CH$_2$-CH$_2$-COOTFP | H | COOH |
| I | MOM $\propto$-CH$_2$COOH | H | H | CH$_2$-CH$_2$-COOTFP |

| Compound | PG | R | R' | R" |
|---|---|---|---|---|
| A | THP | H | H | COOTFP |
| B | EOE | H | H | COOTFP |
| C | EOE | H | H | CH$_2$-CH$_2$-COOTFP |
| D | i-PrCO | CH$_2$-COOH | H | CH$_2$-CH$_2$-COOTFP |
| E | i-PrCO | CH$_2$-COOH | CH$_2$-COOH | CH$_2$-CH$_2$-COOTFP |
| F | i-PrCO | CH$_2$-CH$_2$-COOH | CH$_2$-COOH | CH$_2$-CH$_2$-COOTFP |
| G | Acm | H | H | COOH |
| H | Acm | CH$_2$-CH$_2$-CH$_2$-COOTFP | H | COOH |
| I | MOM | H | H | CH$_2$-CH$_2$-COOTFP |
|   | ∝-CH$_2$COOH | | | |

*Figure 1*

CHELATING COMPOUNDS FOR METAL-RADIONUCLIDE LABELED PROTEINS

CROSS-REFERENCE TO RELATED APPLICATIONS

This application is a continuation-in-part of application Ser. No. 031,440, filed Mar. 26, 1987.

BACKGROUND OF THE INVENTION

1. Field of the Invention

This invention relates to radionuclide-labeled biological substances useful in the fields of diagnosis and therapy and is more particularly related to metal-chelating compounds in which the donor atoms are nitrogen and sulfur.

2. Description of the Background

Radiolabeled compounds are important tools in medical diagnosis and treatment. Such compounds are employed in a variety of techniques including the diagnosis of deep venous thrombi, the study of lymph node pathology, and the detection, staging and treatment of neoplasms. A number of these compounds employ metal radionuclides such as technetium-99m. When employing radionuclides for in vivo administration, it is desirable that the radionuclide localize in a target organ or cancer site. Therefore, radionuclides are usually formulated to provide preferential binding to or absorption by the particular organ or tissue. There is considerable interest in being able to accurately direct a radionuclide to a preselected site to reduce background radiation directed to surrounding or distant tissue, reduce the dosage, minimize background for in vivo imaging, and minimize undesirable side effects. Toward this end, methods involving specific ligands or receptors to which the radionuclide may be conjugated are of interest.

DESCRIPTION OF RELEVANT LITERATURE

Publications of interest include Khaw et al., *J. Nucl. Med.* (1982) 23:1011; Rhodes, B. A., *Sem. Nucl. Med.* (1974) 4:281; Davison et al., *Inorg. Chem.* (1981) 20:1629; and Byrne and Tolman, *J. Nucl. Med.* (1983) 24:126. See particularly Fritzberg et al., id. (1981) 22:258; and Fritzberg et al., id. (1982) 23:17 for descriptions of mercaptoacetyl derivatives of ethylene diaminecarboxylic acid derivatives. See also U.S. Pat. No. 4,444,690.

Copending application Ser. No. 624,098, filed June 25, 1984, discloses technetium derivatives of mercaptoacetylglycylgylcylglycine for scintographic procedures and for evaluating renal function. Copending application Ser. Nos. 07/065,011 and 07/065,017 disclose metal-radionuclide-labeled proteins for diagnosis and therapy wherein the metal chelating compounds are dithiodiamidocarboxylic acids and derivatives thereof.

SUMMARY OF THE INVENTION

Metal-radionuclide-labeled proteins, carbohydrates, and glycoproteins are provided for the diagnosis and treatment of a variety of pathologic conditions. Specifically chelated radionuclide complexes conjugated to a protein, carbohydrate, or glycoprotein are employed for the diagnosis of physiological conditions, including lymph node pathology, deep venous thrombi and the detection and staging of neoplasms. Chelated radionuclides as protein and glycoprotein conjugates are employed for radiotherapy of tumors.

In particular, the radionuclide-labeled proteins, carbohydrates, and glycoproteins of the present invention are formed from the reaction of functional groups such as an activated carboxylic acid group or a primary amine group of a multidentate chelate with a free or terminal amino group on a protein or with a preformed aldehyde moiety of a carbohydrate or glycoprotein, respectively. The aldehyde moiety can be formed from the reaction of periodate or other oxidizing agent with a sugar unit of a carbohydrate or a glycoprotein. The chelates comprehended by the present invention will generally be multidentate organic compounds with a sulfur atom and three nitrogen atoms ($N_3S$ chelates) being available for bonding to a metal radionuclide such as, for example, $^{99m}TcO^{3+}$, $^{99m}TcO_2^+$, $ReO^{3+}$, or $ReO_2^+$. For the purposes of the instant specification and the appended claims, the term "carbohydrate" will be taken to include carbohydrates (including oligosaccharides), the carbohydrate portion of a glycoprotein, or any other carbohydrate moiety.

DESCRIPTION OF THE SPECIFIC EMBODIMENTS

Improved methods and compositions are provided involving chelate precursors and derivatives for conjugating to proteins, carbohydrates and glycoproteins. The resulting peptide and carbohydrate conjugates, which conjugates are complexed with radionuclides, as well as the use of the conjugates in radioimaging and radiotherapy are also disclosed and discussed.

The metal chelating compounds will be thiotriaza chelators, where the heteroatoms that donate electrons to form bonds with the metal atom or ion are separated by two or three, preferably two, carbon atoms and the sulfur may be substituted or unsubstituted. In one embodiment of the invention, the terminal donor nitrogen atom is joined through a linking group, usually alkylene, to an amino (primary or secondary) group or to a non-oxo-carbonyl (carboxyl or derivative thereof) group, usually an acid or an active ester. The ester will be capable of forming an amide bond with an amino group in an aqueous medium. The chelating compound will also have from 0 to 3 carbonyl groups in the chain, particularly to the left of the nitrogen atom in the S→N direction (i.e., at one or more of the positions designated by "X" in the formula below, thereby forming amide bonds). The chelator generally will have a total of from 8 to 26 carbon atoms, usually 8 to 20 carbon atoms. Various substituents may add more carbon atoms to the chelating compound.

The chelating compound may be linked to a polypeptide or carbohydrate in a variety of ways. If the chelator terminates in a carboxyl group or derivative thereof, the carboxyl group may be activated with carbodiimide and an alcohol to form an active ester or may already contain an active ester group that is reacted with an available amino group of a polypeptide or an amino sugar to form an amide bond. Alternatively, if the chelator terminates in an amino group, the amino group may be used to react with an aldehyde group, which may be derived by glycol cleavage of a sugar with periodate, to form a Schiff's base or cyclic imine or under conditions favoring reductive amination to form a secondary or tertiary amine or cyclic imine linkage.

The metal chelating compounds will have, for the most part, the following formula (I):

wherein:
T is H or a sulfur protecting group;
each X independently represents $H_2$ or O;
each R independently represents a substituent selected from the group consisting of hydrogen; alkyl; geminal dialkyl; a non-alkyl side chain of an amino acid other than cysteine (alkyl side chains being covered when R is an alkyl group); and —$(CH_2)_n$—Z;
Z represents —COOH, a conjugation group, or a targeting compound;
n is an integer of from 1 to about 4; and
R' is $H_2$; —$(CH_2)_n$—Z; or an alkyl group having one or more polar groups substituted thereon;
wherein the compound comprises at least one —$(CH_2)_n$—Z substituent.

When Z is —$NH_2$, n should be at least 2. When Z is other than —COOH, n preferably is 3.

The sulfur protecting group may be selected from alkyl, aryl, acyl (preferably alkanoyl or benzoyl), thioacyl groups having 1 to about 7 carbons, and organothio groups having 1 to about 10 carbons.

For the R groups, the alkyl groups generally contain from 1 to 7 carbons, preferably from 1 to 4 carbons, and most preferably represent methyl.

Examples of substituents Z include, but are not limited to —$NH_2$, —$NHNH_2$, —COOH, a carboxylic ester, an imidate ester, an isothiocyanate group, a maleimide group, other Michael acceptor groups, where $W_1$ is a polypeptide of at least two amino acids and $W_2$ and $W_3$ independently represent a carbohydrate, wherein the nitrogen is bonded to a carbon atom of the carbohydrate. "Carbohydrate" encompasses pure carbohydrates consisting entirely of sugar units as well as glycoproteins and other molecules containing amino acids, nucleic acids, or other moieties in addition to carbohydrate moieties. Usually $W_2$ and $W_3$ will be a carbohydrate, namely a polysaccharide, or the carbohydrate portion of a glycoprotein. Of particular interest are the carbohydrate portions of immunoglobulins and receptors. The bonds to the carbohydrate are formed where at least one saccharide unit either contains or has been oxidized to provide an oxo, e.g., aldehyde group.

The linkage between the carbohydrate and the chelate compound is through a secondary or tertiary amine, depending on the nature of the carbohydrate and the stoichiometry of the reaction between the chelate complex and the carbohydrate to form the imine or amine linkage.

Typically, $W_1$ will be an oligopeptide of at least two amino acids, or a polypeptide of at least about 1,000 molecular weight, usually at least about 2,000 molecular weight, generally less than about 1.6 MDal, more usually less than about 800 KDal. Of particular interest are receptors, e.g., immunoglobulins, either polyclonal or monoclonal antibodies or specific binding fragments thereof, or other naturally occurring receptors, e.g., T-cell receptors. Enzymes, hormones, and other compounds that exhibit specific binding to substrates or cells are also of interest.

T represents hydrogen or a sulfur protecting group. Any suitable sulfur protecting group may be used, including known alkyl, aryl, acyl (preferably alkanoyl or benzoyl), or thioacyl group having from 1 to about 7 carbons; or an organothio group having from 1 to about 10 carbons.

In one embodiment of the invention, the sulfur protecting group, when taken together with the sulfur atom to be protected, is a hemithioacetal group. Suitable hemithioacetals include, but are not limited to, those having the following formulae, wherein the sulfur atom is the sulfur atom of the chelating compound:

Preferred hemithioacetals generally are of the following formula, wherein the sulfur atom is the sulfur atom of the chelating compound:

wherein $R^3$ is a lower alkyl group, preferably of from 2 to 5 carbon atoms, and $R^4$ is a lower alkyl group, preferably of from 1 to 3 carbon atoms. Alternatively, $R^3$ and $R^4$ may be taken together with the carbon atom and the oxygen atom shown in the formula to define a nonaromatic ring, preferably comprising from 3 to 7 carbon atoms in addition to the carbon and oxygen atoms shown in the formula. $R^5$ represents hydrogen or a lower alkyl group wherein the alkyl group preferably is of from 1 to 3 carbon atoms. Examples of such preferred hemithioacetals include, but are not limited to:

Tetrahydrofuranyl    Methoxymethyl    2-methyl-tetrahydrofuranyl

-continued

Tetrahydropyranyl  ethoxyethyl  2-methyl tetrahydropyranyl

Advantages of using hemithioacetal sulfur protecting groups include the fact that a separate step for removal of the sulfur-protective groups is not necessary. The protecting groups are displaced from the compound during the radiolabeling in what is believed to be metal-assisted acid cleavage; i.e., the protective groups are displaced in the presence of the metal radioisotope at an acidic pH, and the radioisotope is bound by the chelating compound. The radiolabeling procedure thus is simplified, which is especially advantageous when the chelating compounds are to be radiolabeled in a hospital laboratory shortly before use. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Such base labile groups include any group which may be destroyed, hydrolyzed, or otherwise adversely affected by exposure to basic pH. Certain protein conjugation groups, including esters, isothiocyanates, maleimides, and other Michael acceptors, among others, are relatively base labile. Thus, a radiolabeled chelate may be prepared, and the protein conjugation group remains intact for subsequent binding of the chelate to a targeting compound (e.g., an antibody).

Alternatively, an acetamidomethyl sulfur-protecting group may be used. This group is represented by the formula:

The acetamidomethyl group is displaced from the chelating compound during radiolabeling conducted at about 50° C. in a reaction mixture having a pH of about 3 to 6. The use of an acetamidomethyl group generally improves the water solubility of the chelating compound, which is desirable when the compound is to be attached to a protein or other biological targeting moiety prior to radiolabeling. Aqueous reaction mixtures are preferred for protein conjugation reactions, since organic solvents may denature or otherwise damage the protein.

A variety of other sulfur protecting groups may be used, some of which are described in Example X below.

The preferred chelate compounds according to the invention will generally have the following formula (II):

wherein:
M is a radionuclide ion, to which 1 or 2 oxygen atoms may be bonded, especially if the metal is Tc or Re; and the other symbols are as described for the compound of formula (I) above.

A variety of metal ions or complex ions may be employed as the radionuclide. These metals include, but are not limited to, copper, e.g., $^{64}$Cu and $^{67}$Cu; technetium, e.g., $^{99m}$Tc; rhenium, e.g., $^{186}$Re and $^{188}$Re; lead, e.g., $^{203}$Pb and $^{212}$Pb; palladium, e.g., $^{109}$Pd; bismuth, e.g., $^{212}$Bi, and gold, e.g., $^{198}$Au. The metal may be present as an ion, e.g., $^{64}$Cu$^{2+}$ and $^{67}$Cu$^{2+}$ (copper may end up in S-containing ligands as Cu+) or as an oxidized form, e.g., 99mTcO$_3$+, $^{186}$ or $^{188}$ReO$^{3+}$ when incorporated in the chelate compounds.

The dashed lines in the formula presented for the chelate compounds of the invention represent four coordinate covalent bonds, between the metal radionuclide M and the sulfur and the three nitrogen atoms shown in the formula.

Thus, the metal radionuclide is bound through relatively stable bonds in the chelate compounds of the invention.

The polypeptide or carbohydrate compounds attached to the chelator may be varied widely, depending upon the nature of the use of the radionuclide bound to the chelator. The carbohydrate may be a carbohydrate compound such as a polysaccharide, a glycoprotein, or other compounds comprising a carbohydrate moiety, as described above.

The polypeptides may be ligands or receptors, for example. Ligands may include such a variety of compounds as polypeptides, hormones, lymphokines, growth factors, peptide or carbohydrate substrates, particularly compounds binding to surface membrane receptors, where the complex may remain bound to the surface or become endocytosed. Among receptors are surface membrane receptors, antibodies, enzymes, naturally occurring receptors, lectins, and the like. Of particular interest are immunoglobulin-like compounds or binding fragments thereof, e.g., Fab, F(ab')$_2$, and F$_V$ fragments of antibodies, and T-cell receptors.

Thus, the chelating compounds of the present invention are attached to a targeting compound (usually one of the above-identified polypeptides or carbohydrates) which serves to deliver the radionuclide chelate to a desired target site within a mammalian or human host. As used herein, the term "polypeptide" includes polypeptides, proteins, or fragments thereof. These proteins and polypeptides may be modified as long as the biological activity necessary for the intended diagnostic or therapeutic application of the radiolabeled polypeptide is retained. For example, a modified antibody or fragment thereof may be used as long as binding to the desired antigen still occurs. Modified proteins may be produced using such techniques as genetic engineering or protein engineering.

The targeting compound binds to a desired target site in vivo, thereby delivering the diagnostic or therapeutic radionuclide to the target site. An example of a target site is a cancer site. Many antigens associated with various types of cancer cells have been identified, and monoclonal antibodies specific for a number of these cancer cell-associated antigens also are known. Such antibodies are examples of the many polypeptides suitable for use as targeting compounds. Among the monoclonal antibodies that bind to cancer cells are anti-TAC, or other interleukin-2 receptor antibodies; 9.2.27 and NR-M1-05 to the 250 kilodalton human melanoma-associated proteoglycan; NR-Lu-10 to 37–40 kilodalton pancarcinoma glycoprotein; and $OVB_3$ to an as yet unidentified tumor-associated antigen.

The chelating compound may be radiolabeled to form the corresponding radionuclide metal chelate, and the chelate subsequently is attached to the targeting moiety in the "preformed chelate approach." An alternative approach to preparing radiolabeled targeting moieties is the "post-formed chelate approach" in which the chelating compound is first attached to the protein or carbohydrate targeting molecule. The resulting conjugate is then reacted with a radionuclide metal to form a radionuclide metal chelate bound to the targeting molecule.

The conjugation group "Z" is a functional group which will react with a group on a desired targeting compound to bind the chelate or chelating compound thereto. The conjugation group chosen for use will vary according to the nature of the targeting compound (e.g., whether the targeting compound is a protein or a carbohydrate).

Proteins contain a variety of functional groups; e.g., carboxylic acid (COOH) or free amine (—$NH_2$) groups, which are available for reaction with a suitable functional group "Z" on a chelator to bind the chelator to the protein. For example, an active ester on the chelator reacts with free amine groups on lysine residues of proteins to form amide bonds. Alternatively, the protein and/or chelator may be derivatized to expose or attach additional reactive functional groups. The derivatization may involve attachment of any of a number of linker molecules such as those available from Pierce Chemical Company, Rockford, Ill. (See the Pierce 1986–87 General Catalog, pages 313-354.) Alternatively, the derivatization may involve chemical treatment of the protein (which may be an antibody). Procedures for generation of free sulfhydryl groups on antibodies or antibody fragments also are known (See U.S. Pat. No. 4,659,839.) Maleimide conjugation groups on a chelator are reactive with the sulfhydryl (thiol) groups.

Alternatively, when the targeting compound is a carbohydrate, derivatization may involve chemical treatment of the carbohydrate; e.g., glycol cleavage of the sugar moiety of a glycoprotein antibody with periodate to generate free aldehyde groups The free aldehyde groups on the antibody may be reacted with free amine or hydrazine conjugation groups on the chelator to bind the chelator thereto. (See U.S. Pat. No. 4,671,958.)

Among the preferred conjugation groups for reaction with polypeptide targeting compounds are esters. The esters which may be utilized as conjugation groups represented by "Z" are those esters which provide a covalent, amide linkage with a polypeptide in an aqueous medium. One or another of the reactive esters may be preferred, depending upon the particular radionuclide, the protein, and the conditions for conjugation, as is understood in the art of peptide chemistry. Common esters which find use are o- and p- nitrophenyl, 2-chloro-4-nitrophenyl, cyanomethyl, 2-mercaptopyridyl, hydroxybenztriazole, N-hydroxy succinimide, trichlorophenyl, tetrafluorophenyl, thiophenyl, tetrafluorothiophenyl, o-nitro-p-sulfophenyl, N-hydroxy phthalimide and the like. For the most part, the esters will be formed from the reaction of the carboxylate with an activated phenol, particularly nitro-activated phenols, or a cyclic compound based on hydroxylamine. As other hydroxylic compounds become available, these also may find use in this invention. Imidate esters, such as methyl imidate can be used to give amidine linkages.

The chelators are synthesized from tripeptides such as glycylglycylglycine and S-protected active esters of acetic acid. For example, N-hydroxy succinimide S-benzoylthioacetylglycylglycylglycine (S-benzoyl $MAG_3$). Amino acids comprising various side chains may be employed in the synthesis of the compounds of the invention.

Depending upon the particular metal, various conditions and techniques will be employed for preparing the metal chelate. To prepare the technetium chelate, the chelating compound as a carboxylate, activated ester, or amine is combined with a pertechnetate solution in the presence of a reducing agent, e.g., stannous ion or dithionite under conventional conditions, whereby the technetium chelate is formed as a stable salt. The rhenium chelate may be formed from different routes. For example, by reducing perrhenate to rhenium (IV) hexachloride employing hypophosphorous acid and concentrated HCl at 95° C., rhenium hexachloride is formed. The rhenium hexachloride is then converted to the rhenium dioxo diethylenediamine chloride in 90% ethylenediamine at room temperature. At a basic pH in the presence of the subject chelating agents, the rhenium dioxo diethylenediamine chloride exchanges rapidly with the $N_3S$ chelate.

For use in labeling large peptides and proteins, formation of a metal complex with a conjugating group included is preferable. This preformed approach allows exchange of the metal ion between the inorganic complex in which the metal ion is initially found and the chelate to occur under controlled conditions. Exchange of radioactive metal from a labile inorganic complex to a chelator already conjugated to antibody (the post-formed approach) results in variable amounts of non-specifically bound radioactivity caused by electron donor groups (nitrogen, oxygen, and sulfur atoms) on the antibody or other large protein.

For the preformed chelate approach, the chelated carboxylic acids may be present as an ester or esterified in accordance with conventional means. With the ester, a labile complex such as Tc-99m gluconate can be prepared and used to exchange with the $N_3S$ activated ester forming a radionuclide complex suitable for protein conjugation. Alternatively, the carboxylic acid may be activated by employing a water soluble carbodiimide, e.g., EDCI, in an aqueous medium in the presence of at least a stoichiometric amount, preferably an excess of the esterifying hydroxylic compound. A suitably buffered aqueous medium may be employed. Any unreacted carbodiimide can be converted to urea by adding acetate. The aqueous medium may then be used directly without further purification for conjugation to the polypeptide. Preferably, polypeptide (e.g., protein) will be added to the ester-containing aqueous medium at a convenient concentration at a mildly alkaline pH, generally in greater than about 7.5 and less than about 10.5, and the reaction allowed to proceed for a sufficient time for all of the active ester to either react with the polypeptide or be active ester to either react with the polypeptide or be substantially completely hydrolyzed. Usually, the time will be less than about 6 hr and more than about 1 min, with temperatures ranging from about 0° to 50° C., usually not exceeding about 40° C. The particular conditions will be selected in accordance with the particular activated ester, the pH, the activity of the polypeptide, and the like.

The carbohydrate portion of glycoproteins can be oxidized with periodate to give aldehyde groups that can be used for conjugation. The protein is buffered in acetate at pH 5.5 and reacted with sodium periodate for about 1 min at room temperature. After quenching with glycerol the protein is purified by passage through a gel filtration column.

The amine may be condensed with the dialdehyde in the presence of mild acid, preferably in an aqueous medium with sodium cyanoborohydride to provide for reductive amination.

It may be more convenient for some applications to conjugate the chelating agent ($N_3S$) to the polypeptide or carbohydrate in the absence of the metal ion. For example, since some of the radionuclides contemplated by the present invention (e.g., $^{99m}Tc$) have relatively short half-lives, it may be desirable to prepare the chelating-agent-conjugated polypeptide or carbohydrate moiety and then, shortly prior to administration, react the chelating compound-conjugated polypeptide or carbohydrate moiety with the radionuclide of interest. For example, the carboxylic acid group would be linked to the polypeptide to form an amide linkage, followed by the addition of the metal, in a weakly complexed form. Alternatively, for chelating compounds having a free primary amine group, the $N_3S$ chelating compounds could be linked to a carbohydrate moiety, as discussed above, by linking the primary amine to the carbohydrate moiety following periodate treatment of the carbohydrate moiety, under mild reducing conditions to form a secondary or tertiary amine linkage; this procedure would then be followed by the appropriate reaction with the radionuclide to form the desired radiolabeled carbohydrate moiety.

Initially, as mentioned previously, the metal ion might non-specifically as well as specifically bind to the polypeptide or carbohydrate. However, the $N_3S$ ligand center should form chelates of higher stability than the non-specific sites, and the metal ions under equilibrium conditions would migrate to the $N_3S$ chelating group. Those metal ions not bound to the $N_3S$ chelating group could be washed away under mild conditions with a chelating agent, e.g., EDTA, or a non-ionic detergent. Conveniently, the metal ion could be added as a weakly chelated ion or in the presence of a weakly chelating group, such as a uronate, e.g., gluconate, or tartrate.

The subject chelates will be administered to the mammalian host, normally by injection, intravenously, intraarterially, peritoneally, intratumorally, or the like, depending upon the particular site at which the radionuclide is desired. Generally, from about 0.1 to 2 ml will be injected into a host, depending upon the size of the host, with about 0.001 to 50 uCi/kg of host. For human hosts, the dosage will usually be about 10–50 mCi/70 kg host, more usually about 25–35 mCi/70 kg host. For lower mammals, e.g., mice, 1–50 uCi will be used for biodistribution studies, while up to or greater than 500 uCi will be used for imaging studies. After administration of the radionuclide, depending upon its purpose, the host may be treated in various ways for detection or therapy by detection of the radioactive emissions from the site or sites where the radionuclide specifically binds.

The following examples are offered by way of illustration and not by way of limitation.

Example I

Synthesis of S protected mercaptoacetylglycylglycylglycine ($RMAG_3$)

To a solution of glycylglycylglycine in acetonitrile-water (80:20) containing triethylamine (10 ml of solvent and 3 equivalents of $NEt_3$ per mmol of gly-gly-gly-OH), S-protected thioglycolic acid succinimidate ester (1 equivalent) was added in one lot. The solution was stirred for 2 hours at room temperature. Solvents were removed in vacuo, and the residue was dissolved in 5–10 ml of water and acidified in hydrochloric acid (pH=3–4). The product crystallized on standing, in the case of (a) and (b).

In case (c), no precipitate was obtained. The aqueous solution was evaporated to dryness and the product was isolated by silica-gel flash chromatography using $CH_3CN: H_2O$ (95:5) as the eluent.

The reaction was run five times using different protecting groups.

$Ra = C_6H_5CO$ $Rb = p\text{-COOtBu}(C_6H_4)\text{---CO---}$

Example II

Preparation of S-benzoyl-MAG-3 tetrafluorophenyl ester

To a suspension of 1.1 g (3 mmol) of S-benzoyl-$MAG_3$ in 150 mL of anhydrous tetrahydrofuran, 0.5 g (3 mmol) of 2,3,5,6-tetrafluorophenol and 0.68 g (3.3 mmol) of N,N'-dicyclohexylcarbodiimide were added and stirred for 72 hours at room temperature.

Approximately 100 ml of the solvent was removed under reduced pressure and the precipitated dicyclohexylurea was filtered. The filtrate was evaporated to dryness and the residue was dissolved in ~50 ml of warm acetonitrile and allowed to cool to room temperature. The crystallized solid (mostly dicyclohexylurea along with some product) was filtered and the filtrate was concentrated to about 30 ml and cooled in an icebath. The crystallized solid (some more dicyclohexylurea was filtered).

The filtrate was evaporated to ~5 ml and the product was precipitated by addition of anhydrous ether to give 0.21 g of the product, mp: 172°–4° C.

NMR (DMSO-$d_6$): δ 3.72–3.98 (m and s, 6, gly $CH_2X2$, S-$CH_2$), 4.36 (d,2,gly $CH_2$), 7.62–8.8 (m,9, 3XNH, $C_6H_5$, p-CH(TFP)).

Example IIIa

Synthesis of S-benzoyl MAG$_3$ tetrafluorophenyl active ester

φCOSCH$_2$-CO-Gly-Gly-Gly-OH + 2,3,5,6-TFP-OH → φCOSCH$_2$COglygly-gly-o-2,3,5,6-TFP To a solution of the MAG$_3$ derivative in anhydrous THF (20 mL/mmol), equimolar amounts of tetrafluorophenol and dicyclohexylcarbodiimide were added. The mixture was stirred overnight at room temperature. Dicyclohexylurea was filtered off, and the filtrate was dissolved in $CH_2Cl_2$. The solution was washed with water, dried over anhydrous $Na_2SO_4$ and evaporated to about one-third of the original volume. The precipitated solid was removed, and the filtrate was evaporated to obtain the active ester (Ra, Rb) in 55–60% yield.

Removal of t-butyl groups (in the case of Rb) was accomplished by stirring the above product in anhydrous trifluoroacetic acid (5 ml of TFA/1 mmol). The acid was removed in vacuo. Addition of cold water (5–10 ml) gave the product, which was filtered and dried under vacuum.

In the case of Rc, the reaction was conducted in a mixture of $CH_3CN$: $H_2O$ (4:1; 20 ml/mmol). To a solution of Rc (mmol) in $CH_3CN$: $H_2O$ was added 3 mmol of 2',3',5',6'-tetrafluorophenol, and 3 mmol of 1-(3-dimethylaminopropyl)-3-ethylcarbodiimide hydrochloride was added and stirred for 8 hours. The solvent was removed and extracted with ethyl acetate. The organic layer was dried over $MgSO_4$ and evaporated to give an oil. Trituration with ether gave the tetrafluorophenyl ester. The N-hydroxysuccinimide ester of Rc is prepared in a similar reaction.

Example IIIb

THP-S-CH$_2$COGly-Gly-Gly-OSuCC.→THP-S-CH$_2$-CO-Gly-Gly-Gly-CONHNH$_2$

To a solution of above succinimidate ester in THF (5 ml/mmol), 0.2 mL of hydrazine is added and stirred for 3–4 hours. The solvent is removed and product is isolated by silica gel chromatography. THP indicates a tetrahydropyranyl S-protecting group.

In a similar set of reactions, other MAG$_3$ derivatives, where sulfur is protected as hemithioacetals are prepared (Rd, Re).

Example IIIc

(i) To a solution of tBoc-Gly-Gly-Gly-NH$_2$ in (25 mL/mmol) of THF, 9 mL of BH$_3$ THF is added and the solution is refluxed for overnight (12–15 hours). Two mL of ethanol is added and the solution is evaporated to dryness. This process is repeated three more times and the resulting oil is dried to give a powder.

(ii) To a solution of the protected amine in anhydrous THF (5 mL/mmol) equimolar amount of S-benzoylthioglycolic acid succinimidate ester is added. The solution is stirred for 3–4 hours. TLC shows one major component along with minor impurities. The major component is purified by silica gel column chromatography (EtoAc: $CH_3OH$: $NEt_3$).

(iii) One mmol of the above protected compound is stirred with 5 mL of anhydrous trifluoroacetic acid. After 2–3 hours of stirring the trifluoroacetic acid is evaporated. The oily product is dissolved in ethanol and evaporated to dryness. This process is repeated two times. Ethanol containing 5–6 equivalents of dissolved hydrogen chloride was added and evaporated to dryness to give the product as a viscous oil which solidified upon adding ether.

Example IV

Preparation of Tc-99m MAG$_3$-IgG Antibody

In 0.10 mL of 1.0 M carbonate buffer pH 12.0 was dissolved 25 ug of S-benzoylmercaptoglycylglycylglycine. Then 75 mCi of Tc-99m pertechnetate was added in about 1.0 mL followed by 1.0 mg of freshly dissolved sodium dithionite (10 mg/mL). The mixture was heated at 100°±4° C. for 3 min, then cooled in ice-bath for 5 min, to give 90–95% Tc-99m MAG$_3$ as determined by ITLC ($CH_3CN$ solvent: 95% at origin; 10% ammonium acetate $CH_3OH$ (1:1): 99% solvent front); anion exchange HPLC (Beckman AX, 10 micron 0.01M Na$_2$SO$_4$/0.01M Na$_3$PO$_4$, pH 7.0) retention volume 5.4 mL; revere phase HPLC (Beckman ODS, 5 micron 2% $CH_3CN$/0.01M Na$_3$PO$_4$ pH 7.0) retention volume 7.6 mL).

The Tc-99m complex in carboxylate form was then esterified: 0.20 mL 1N HCl, 0.30 mL of 0.2M phosphate buffer pH 6.0, 10.0 mg 2,3,5,6-tetrafluorophenol (TFP) in 0.10 mL 90% $CH_3CN$, 12.5 mg of EDC in 0.10 mL of 90% $CH_3CN$, and the reaction was mixed at room temperature (20°±2° C.) for 1 hr. At this point, 60–75% of the radioactivity was Tc-99m MAG$_3$-TFP ester as determined by ITLC ($CH_3CN$ solvent: 60–75% at solvent front); anion exchange HPLC (Beckman AX, 10 micron 0.01M $Na_2SO_4$/0.01M $Na_3PO_4$ pH 7.0) retention volume 3.0 mL; reverse phase HPLC (Beckman ODS, 5 micron 34% $CH_3CN$/0.01M $Na_3PO_4$ pH 7.0) retention volume 6.2 mL. The preparation was purified using a $C_{18}$ Baker column. The reaction-mixture was loaded in the column, washed 2 times with water and then 8 times with 2.0 mL of 10% $C_2H_5OH$/0.01M $Na_3PO_4$ pH 7.0. The product was eluted with $CH_3CN$. The radiochemical yields are 50-60% in Tc-99m $MAG_3$-TFP. The $CH_3CN$ was removed, and the Tc-99m $MAG_3$-TFP was ready for conjugation.

The conjugation of the complex active ester was carried out by adding a 1.2 mg/mL solution of antimelanoma IgG in 0.2M phosphate buffer pH 9.5 to the residue containing the Tc-99m activity. After 30 min, 40-50% of the radioactivity was bound to the antibody. Passage through a PD-10 gel filtration column gave 97% pure Tc-99m $MAG_3$-Antibody.

Example V

Preparation of active ester of MAGGG (Succinimidylbenzoylmercaptoacetylglycylglycylglycine)

In a 50 ml round bottom flask, 0.37 g (1 mmole) of benzoylmercaptoacetylglycylglycylglycine and 0.126 g (1.1 mmole) of N-hydroxy succinimide are dissolved in approximately 25 mL of tetrahydrofuran and cooled to 5°-10° C. in an ice bath. To this solution, 0.23 g (1.1 mmole) of N,N'-dicyclohexylcarbodiimide is added. The solution is allowed to warm to room temperature and is stirred for 48 hours and the course of the reaction followed by TLC. The precipitate is removed by filtering; the filtered solution is evaporated to dryness under vacuum. The residue is redissolved in 50-60 mL of dichloromethane; this solution is filtered and evaporated to dryness under vacuum. The residue is redissolved in 5-6 mL ethanol with warming and allowed to crystallize for 3-4 hours. The crystals of product succinimidyl-MAGGG are recovered by filtration.

Example VI

Preparation of antibody chelating compound conjugate

A stock solution of tetrafluorophenyl-MAGGG is prepared by dissolving 4.25 mg in 5.0 ml of DMF. 0.060 ml of this solution was added to 0.54 ml of a 5.5 mg/ml solution of monoclonal antibody in 0.10M phosphate, 0.15M NaCl at pH 7.0. Ligand to antibody offering ratio was 50:1. After stirring for 3 hours at room temperature the reaction mixture was purified by passage through a PD-10 gel filtration column.

The entire reaction mixture is purified on Sephadex G-25 previously equilibrated with PBS (1.5cm×5.0 cm plastic column, eluted with PBS). 1.2 mL fractions are collected. Those fraction with an absorbance (280 nm) greater than 0.1 are combined. The combined fractions are concentrated in an Amicon filter with an Amicon PM10 membrane at 4 psi to a final volume of 0.5 to 1.0 ml.

The amount of chelating compound bound to the antibody is conveniently determined by removing the benzoyl group from the ligand with 0.1N NaOH and reacting the resulting free sulfhydryl groups with Ellman's reagent.

Example VII

Analysis of Chelating Compound Conjugation to Monoclonal Antibody

Samples of chelating-compound-conjugated monoclonal antibody (Example VI) are prepared by adding up to 400 uL to a test tube and adjusting the volume to 400 uL with oxygen-free water, if necessary. If necessary, the samples, as prepared according to Example VI, can be diluted with oxygen-free water. Phosphate buffer (500 uL; 0.1M sodium phosphate, 1 mM EDT, pH 7.27) and 100 u of 0.5M hydroxylamine hydrochloride (HA; prepared with oxygen-free water) are added to the test tubes which are then allowed to incubate at room temperature for one hour. Twenty (20) uL of a solution of 5 uL of buffer and 9.0 uL of Ellman's reagent (DTNB; 5,5'-dithiobis(2-nitrobenzoic acid)) is added; after five minutes, the absorbance of the reaction mixture is determined at 413 nm. The amount of chelating compound conjugated to monoclonal antibody can be determined in either of two ways. A blank prepared as above, omitting the chelating compound-conjugated antibody, can be prepared and analyzed at 412 nm. The published extinction coefficient (Riddles, et al., 94 Anal. Biochem. 75 (1979)) can be used to calculate the concentration of free thiol by the following formula:

[thiol concentration] = ($A_{412}$ (sample) −

$A_{412}$ (blank)) × (dilution factor)/14,150 $M^{-1}$.

Alternatively, a standard curve can be constructed. A 0.25 mM solution of high purity cysteine is prepared in the buffer used for the chelating compound conjugation analysis (this standard solution should be prepared fresh daily). Serial dilutions of the cysteine standard are reacted with HA and DTNB as outlined above, and a standard curve of moles of cysteine vs. absorbance at 412 nm is constructed. The amount of chelating compound conjugated to the antibody can be determined directly from this standard curve.

Example VIII

Radiolabeling of chelating-compound conjugated antibody a. Preparation of Technetium-99m Tartrate To a vial of stannous tartrate solution containing 0.10 mg of stannous chloride and 75 mg of sodium tartrate in 0.60 ml was added 0.50 ml of Tc-99m sodium pertechnetate (2-4 mg). The solution is equilibrated at room temperature for three min. If desired, the extent of reaction to form Technetium-99m tartrate can be determined by TLC.

Two Gelman ITLC-SG strips are spotted at the (marked) origin with small drops of the radioactive solution prepared above. Immediately, one of the strips is developed with saline solution; after drying the initial spot under a stream of nitrogen, the other strip is developed in methylethyl ketone (MEK). After the solvent fronts have traveled 75% of the length of the strips, the strips are removed from the development solutions and the solvent front is marked. The strips are cut midway between the origin and the solvent front. The radioactivity on each of the four pieces is determined by standard counting techniques. Since the Rf value of sodium pertechnetate is 1 in the MEK system and 1 in the saline system, and the Rf of technetium tartrate is 0 in the MEK system and 1 in the saline system, and the Rf value of technetium dioxide is 0 in both systems, the fraction of Tc-99m tartrate can be determined by the following equation:

$$\text{fraction (Tc-99m tartrate)} = 1.00 - \frac{C_1 \text{ MEK}}{C_o \text{MEK} + C_1 \text{ MEK}} + \frac{C_o \text{ saline}}{C_o \text{ saline} + C_1 \text{ saline}}$$

where $C_1$ and $C_0$ are the radioactivity counts at the solvent front and origin, respectively, for the two solvents. The Tc-99m tartrate can be used if the fraction of Tc-99m tartrate is 0.85 or more.

b. Reaction of Tc-99m tartrate with chelating compound-conjugated antibody

The antibody MAGGG conjugate in Example 6 (0.10 mg in 0.40 ml of PBS buffer at pH 8) was reacted with Tc099m tartrate (0.10 ml, 0.5–2 mg) for 60 min at 50° C. At that time, 80% of the Tc-99m radioactivity was bound to the antibody. Immunoactivity of the preparation as determined radioactivity bound to melanoma tumor cells was determined to be 84% after correction for nonprotein bound radioactivity.

Example IX

A comparative study was carried out in animals to determine the relative ability of $^{99m}$Tc-MAG$_3$-NRML-05 Fab and $^{99m}$Tc-N$_2$S$_2$-NRML-05 to labeled tumors in mice. These designations refer to the different chelating agents attached to antibody Fab fragments. The designation NRML-05 is a laboratory designation for a specific antibody to a melanoma tumor. MAG$_3$ is the N$_3$S chelating agent described in the preceding examples N$_2$S$_2$ is a designation for a comparison chelating agent having two sulfurs and two nitrogens as electron donating atoms The specific compound is 4,5-bis(2'-thioacetamido)pentanoic acid.

Groups of four mice were injected with similar doses of technetium-labeled reagents. Nude mice bearing melanoma xenographs were utilized. Mice were sacrificed 20 hours post-injection, and samples were counted in a gamma counter. Two tables are set forth below presenting the data obtained. The first table shows percent dose/gram of tissue tested. The second table shows the tumor/tissue ratios (obtained by dividing the percent dose/gram present in a tumor by the percent dose/gram of the individual tissue types.

TABLE 1

| Tissue | % Dose/Gram | | | |
|---|---|---|---|---|
| | MAG$_3$-Label | | N$_2$S$_2$-Label | |
| | Avg. | Std. Dev. | Avg. | Std. Dev. |
| Blood | 0.16 | 0.01 | 0.20 | 0.03 |
| Tail | 0.44 | 0.11 | 0.96 | 0.89 |
| Tumor | 2.28 | 0.52 | 3.02 | 1.12 |
| Skin | 0.09 | 0.01 | 0.08 | 0.03 |
| Muscle | 0.04 | 0.00 | 0.35 | 0.52 |
| Bone | 0.12 | 0.03 | 1.02 | 1.57 |
| Lung | 0.78 | 0.26 | 10.23 | 5.49 |
| Liver | 0.26 | 0.01 | 0.88 | 0.34 |
| Spleen | 0.26 | 0.07 | 0.57 | 0.31 |
| Stomach | 0.23 | 0.14 | 0.76 | 0.51 |
| Neck | 0.05 | 0.01 | 0.12 | 0.05 |
| Kidney | 1.42 | 0.21 | 0.43 | 0.07 |
| Intestine | 0.50 | 0.33 | 0.38 | 0.17 |

TABLE 2

| Tissue | Tumor/Tissue Ratios | |
|---|---|---|
| | MAG$_3$-Label | N$_2$S$_2$-Label |
| Blood | 14.09 | 14.86 |
| Tail | 5.34 | 4.57 |
| Tumor | 1.00 | 1.00 |
| Skin | 25.63 | 64.93 |
| Muscle | 54.89 | 39.68 |
| Bone | 21.03 | 15.73 |
| Lung | 3.47 | 0.47 |
| Liver | 8.71 | 3.66 |
| Spleen | 9.98 | 31.96 |
| Stomach | 11.84 | 36.73 |
| Neck | 42.54 | 29.86 |
| Kidney | 1.64 | 6.94 |
| Intestine | 5.61 | 9.35 |

The data indicates good targeting in tumor tissue. When MAG$_3$ is utilized as a chelating agent, the tumor has the highest percentage dose per gram of any tissues tested. In this comparative study, use of the N$_2$S$_2$ chelator results in a greater percentage of the dose present in the lungs than in the tumor on a per gram basis. Other studies prior to and since this study show the lung concentration to be unusually high in this instance. However, other tissue concentrations are in agreement with usual values. The excretion pattern of the Tc-99m-MAG$_3$ chelate conjugate is also better than that of the N$_2$S$_2$ chelate. This shown by lower liver and spleen concentrations for the Tc-99m-MAG$_3$ chelate conjugate than for the N$_2$S$_2$ linked conjugate. Additionally, the low stomach levels for the MAG$_3$ material is indicative of high stability, since loss of Tc-99m as pertechnetate is seen as a relatively high level of radioactivity in stomach tissue.

Example X

Figure 1:
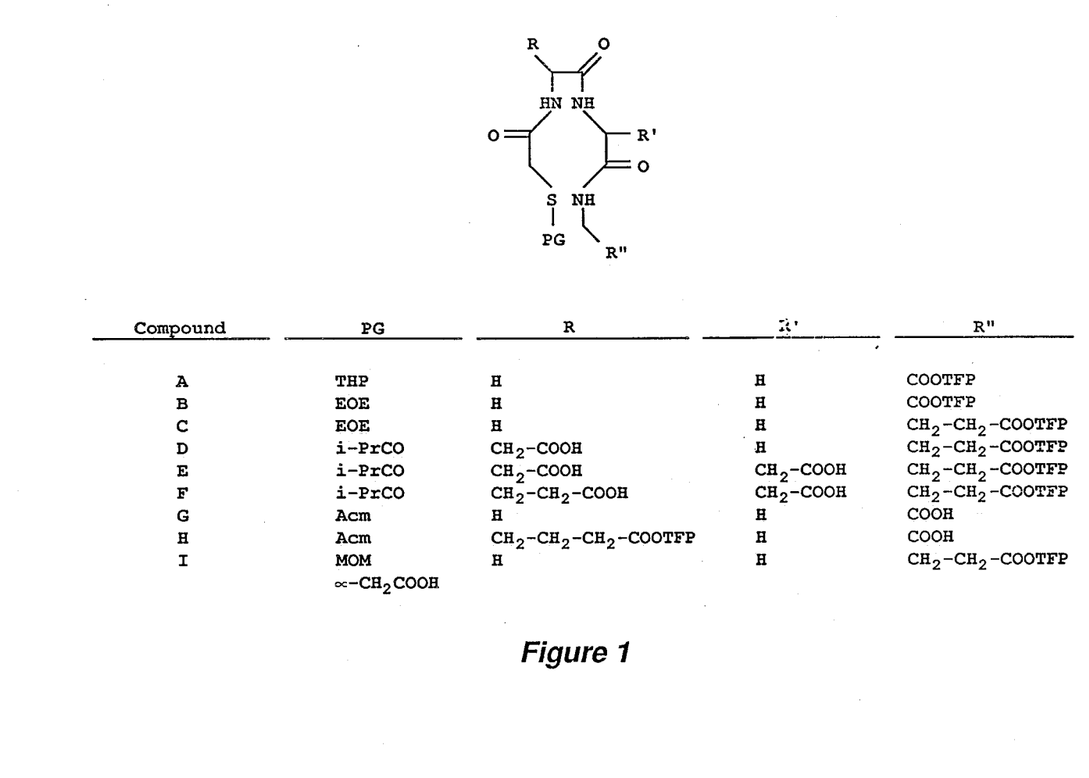
FIGS. 1A to 1I depict the chemical structures of nine "$N_3S$" chelating compounds of the invention. The sulfur protecting group (PG), as well as the position of the protein conjugation group and other substituents, varies among the nine compounds represented.

Nine additional N$_3$S chelating compounds of the invention were synthesized. The chemical structures of these compounds are represented in FIG. 1, wherein FIGS. 1A through 1I correspond to the nine compounds designated A through I. The sulfur protecting group (PG) and the three substituents represented as R, R', and R" are shown for each compound (by reading horizontally across the chart for each compound).

The abbreviations for the sulfur protecting groups (PG) in FIG. 1 represent the following groups, wherein the sulfur atom shown is the sulfur atom of the chelating compound:

Tetrahydropyranyl (THP)  Ethoxyethyl (EOE)  i-PrCO

Acetamidomethyl
(ACM)

Methoxymethyl
(MOM)

When the chelating compound comprises a methoxymethyl S-protecting group (as does compound I), the carbon immediately adjacent to the sulfur atom in the chelating compound (the alpha carbon) preferably has the substituent —CH₂COOH attached thereto.

TFP represents a 2,3,5,6-tetrafluorophenyl group. The 2,3,5,6-tetrafluorophenyl ester protein conjugation group preferably is at the terminus of a —(CH₂)₃— spacer when the preformed chelate approach is to be used, to minimize hydrolysis (or displacement) of the TFP group during the radiolabeling reaction. Compounds A and B, in which the TFP is attached to a shorter spacer, are more suitable for the post-formed chelate approach, since the TFP already has reacted with a protein and is no longer subject to hydrolysis during radiolabeling in the post-formed approach.

Preferred chelating compounds include those in which substituent R″ is —COOH.

The compounds are radiolabeled using procedures described above. The radiolabeling reaction conditions (e.g., pH and temperature) will vary according to such factors as the ease of displacement of the particular S-protecting group on the compound, as described above.

By using the compounds of the subject invention, one can rapidly conjugate proteins, carbohydrates, and glycoproteins to provide radionuclide substituted reagents for use in vivo. The reagents can be provided in pure form and in good yield, and the radionuclide metal is stably maintained as a chelate with the protein, carbohydrate, or glycoprotein for use in vivo. Thus, one can safely direct a radionuclide to a desired site, where only low levels of radioactivity will be non-specifically directed and bound.

Although the forgoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

What is claimed is:

1. A compound of the formula:

wherein COOTFP represents a 2,3,5,6-tetrafluorophenyl ester group.

2. A compound of the formula:

wherein COOTFP represents a 2,3,5,6-tetrafluorophenyl ester group.

3. A compound of the formula:

wherein EOE represents an ethoxyethyl sulfur protecting group and COOTFP represents a 2,3,5,6-tetrafluorophenyl ester group.

4. A compound of the formula:

wherein COOTFP represents a 2,3,5,6-tetrafluorophenyl ester group.

5. A compound of the formula:

wherein Acm represents an acetamidomethyl sulfur protecting and COOTFP represents a 2,3,5,6-tetrafluorophenyl ester group.

6. A compound of the formula:

wherein MOM represents a methoxymethyl sulfur protecting group and COOTFP represents a 2,3,5,6-tetrafluorophenyl ester group.

* * * * *

UNITED STATES PATENT AND TRADEMARK OFFICE
CERTIFICATE OF CORRECTION

PATENT NO. : 4,965,392

DATED : October 23, 1990

INVENTOR(S) : Fritzberg et al.

It is certified that error appears in the above-indentified patent and that said Letters Patent is hereby corrected as shown below:

In column 19, line 15 [claim 5], after "protecting" please insert --group--.

Signed and Sealed this

Thirty-first Day of October 1995

Attest:

BRUCE LEHMAN

Attesting Officer     Commissioner of Patents and Trademarks